United States Patent [19]

Hosoya

[11] Patent Number: 4,498,330
[45] Date of Patent: Feb. 12, 1985

[54] GAS DETECTING AND MONITORING DEVICE

[75] Inventor: Toshiro Hosoya, Tokyo, Japan

[73] Assignee: U.S. Industrial Products Co., Norwalk, Calif.

[21] Appl. No.: 376,519

[22] Filed: May 10, 1982

[30] Foreign Application Priority Data

May 15, 1981 [JP] Japan ................................ 56-72918

[51] Int. Cl.³ ........................................... G01N 27/12
[52] U.S. Cl. ...................................... 73/23; 73/27 R
[58] Field of Search ...................... 73/23, 27 R, 204; 422/94, 96, 98; 340/632, 633, 634; 324/DIG. 1, 65 R

[56] References Cited

U.S. PATENT DOCUMENTS

| | | | |
|---|---|---|---|
| 2,759,354 | 8/1956 | Cherry et al. | 73/27 R |
| 3,429,178 | 2/1969 | Durbin | 73/27 R |
| 3,634,757 | 1/1972 | Monomakhoff | 73/27 R |
| 4,164,699 | 8/1979 | Timoshenko et al. | 340/634 |
| 4,202,666 | 5/1980 | Hall et al. | 422/96 |

Primary Examiner—Stephen A. Kreitman
Attorney, Agent, or Firm—Limbach, Limbach & Sutton

[57] ABSTRACT

A gas detecting and monitoring device comprises a bridge circuit including a gas detecting element and a constant-current circuit for feeding a constant current to the gas detecting element. The device further comprises a compensating bridge circuit including at least a part of the gas detecting element. The compensating bridge circuit produces a signal corresponding to the variation of the resistance value of the gas detecting element depending upon the variation of the ambient temperature and feeds the signal to the constant-current circuit to automatically control the current fed to the bridge circuit thereby maintaining the resistance value of the gas detecting element at a constant value. The device may further comprise a correcting circuit including a temperature sensor for sensing the variation of the ambient temperature disposed near the gas detecting element. The correcting circuit feeds the output of the temperature sensor corresponding to the variation of the ambient temperature to the compensating bridge circuit thereby compensating for the variation of the respective circuit components owing to the variation of the ambient temperature.

8 Claims, 6 Drawing Figures

4,498,330

GAS DETECTING AND MONITORING DEVICE

BACKGROUND OF THE INVENTION

1. Field of the Invention

The present invention relates to a gas detecting and monitoring device for detecting and monitoring the presence of inflammable or poisonous gas such as methane gas, hydrogen gas, ammonia gas, LPG or the like.

2. Description of the Prior Art

The gas detecting and monitoring device of this kind, which has been heretofore used, includes an indicating instrument portion arranged at a central monitoring position and gas detecting portions arranged at gas detecting positions at a distance such as few tens meter to 2 kilometer from said central monitoring position, said indicating instrument portion and said gas detecting portions being connected by transmission cables. The construction of the conventional gas detecting and monitoring device of this kind is schematically shown in FIG. 1. As schematically shown in FIG. 1, the gas detecting portion 10 comprises a wheatstone bridge which includes two sides consisting of a detecting element S.B and a compensating element R.B connected in series and other sides consisting of resistors $R_1$, $R_2$ and $R_3$ connected in series. A power source E is connected through a constant-current circuit CR to one ends of said bridge circuit. The potential difference e between the other ends a and b of the bridge circuit is fed through a transmission cable 30 to an indicating instrument portion 20. The detecting element S.B consists of a coil of fine wire of platinum or the like, on which the material responsive to the gas to be detected, for example oxidizing catalyst, is adhered and sintered in the form of beads. The compensating element R.B consists of a coil of same platinum wire as that of the detecting element S.B. on which ceramic material is adhered and sintered, so that the compensating element R.B holds same temperature rise and same resistance value as those of the detecting element S.B in the normal air, and also these elements are formed in same shape. However, the compensating element is different from the detecting element in the point that the former is not responsive to the gas to be detected. In operation of this gas detecting and monitoring device, the current fed to the detecting element S.B and the compensating element R.B is automatically controlled to an optimum value through the constant-current circuit CR and then held at a constant current value, and when the power fed to the detecting element S.B and the compensating element R.B becomes equal to the thermal loss emanating from these elements to the surrounding atmosphere, the temperature of these elements becomes constant and under such condition the potential difference between a and b is made to be zero (by adjusting the variable resistor $R_2$), so that the indicator of the indiating instrument portion 20 indicates zero value. Under such circumstances, if the methane gas, for example, exists and comes into contact with the detecting element S.B, it burns owing to the reaction of the gas with the catalyst, thereby generating heat, and the temperature of the heat thus generated adds to the temperature of the preheated platinum coil, so that the resistance value of the platinum coil increases in accordance with the temperature coefficient thereof. Accordingly, a potential difference between a and b of the bridge circuit appears and said potential difference is indicated on the indicator of the indicating instrument portion 20, thereby detecting the existence of the methane gas. In this case, this potential difference is proportional to the concentration of the existing methane gas.

In the conventional device as described above, the change of the resistance value depending upon the temperature change of the platinum wire which constitutes the elements S.B and R.B is linearly stable, as shown by curve A shown in FIG. 2, under usual conditions. Accordingly, the potential difference appearing between a and b of the bridge circuit is always held at a constant value when the gas concentration is zero, and therefore this bridge circuit is functionally satisfactory. However, the temperatures of the detecting element S.B and the compensating element R.B themselves (the temperatures owing to generation of heat) usually vary, depending upon the current value fed thereto and the resistance values thereof, and it is a usual practice to select such current value that the temperature of the detecting element becomes maximum at a predetermined room temperature (for example 20° C.) and to hold the current value at a predetermined value by means of the constant-current circuit CR. For example, 130-300 mA current is fed to the platinum wire to heat the detecting element to the temperature between 300° and 500° C., and thus it is used under highly sensitive condition. Consequently, it has such disadvantage that the sensitivity and the indicated value of the detecting and monitoring device vary depending upon the variation of the ambient temperature.

The temperature change of the detecting element itself is considered to be produced on the following grounds.

(1) Change of the characteristics of the detecting element itself due to ambient temperature change:

In the open air the temperature varies, for example, in the range between −40° C. (at night and cold time) and +80° C. (at midsummer and daytime), and in the room the temperature varies, for example, in the range between −10° C. (in factory or loading station and at night time) and +50° C. (at working time in daytime). The detecting portion of the device is subjected to the influence of such temperature variation of the outside factor. That is, the temperature of the detecting element itself varies, owing to such temperature variation of the outside factor.

(2) Change of the characteristics of the parts due to ambient temperature change:

The resistance value of the platinum wire, the resistance value of the resistor, the drift of 1C and transistor in the constant-current circuit, the resistance value of the transmission cable connecting the detecting portion and the indicating instrument portion and the like are subjected to the influence of the ambient temperature change.

In general, a detecting element is heated by a constant current, as described above. Consequently, as the ambient temperature becomes higher, the resistance value of the element increases in accordance with the temperature coefficient of platinum, thereby causing a further rise of temperature, and as the ambient temperature becomes lower, the resistance value decreases, thereby causing a further lowering of temperature. In any case, the temperature departs from its optimum value, with the result that the sensitivity and the value of indication of the gas detecting and monitoring device are changed. The relation between such gas sensitivity and the temperature can be represented by the relation between the a-b potential difference of the bridge circuit and the temperature, for example, as shown by the curve B in FIG. 3. Also the relation between this gas sensitivity and the temperature can be represented by the ambient temperature and the indication error as seen on the indicator of the indicating instrument portion, for example, as shown by the curve C in FIG. 4. It will be clear from these curves B and C that even if the allowable range of error as ±3%, the conventional device produces an error beyond such allowable range, and therefore it cannot fully realize its primary purpose of detecting the leakage of inflammable or poisonous gas and foretelling and preventing the occurrence of accidents.

The compensation for such ambient temperature change might be obtained by connecting a thermal responsive semiconductors or the like to the elements of the bridge circuit. However, there is wide variation in characteristics of thermal responsive semiconductors, and therefore this method of compensation needs correction of characteristics of the thermal responsive semiconductors, that is troublesome, and may give rise to the lowering of the sensitivity of the detecting element. Accordingly, this method of compensation cannot be said to be a best method.

It is an object of the present invention to provide a gas detecting and monitoring device which eliminates the disadvantages as described above and which is not susceptible to the influences of the ambient temperature changes and can effect accurate gas detection as all time.

SUMMARY OF THE INVENTION

In accordance with an aspect of the present invention, the above object can be attained by adding a compensating bridge circuit by which the detecting element S.B. and the compensating element R.B of the bridge circuit in the conventional device can hold constant resistance values in irrespective of the ambient temperature change.

In accordance with another aspect of the present invention, the above object can be attained by further providing a correcting circuit for compensating for changes of the characteristics of the components of the bridge circuit depending upon change in ambient temperature.

DESCRIPTION OF THE PREFERRED EMBODIMENTS

Now the invention will be explained more in detail, with reference to the accompanying drawings, particularly FIG. 5 which illustrates a preferred embodiment of the present invention.

Figure 5:
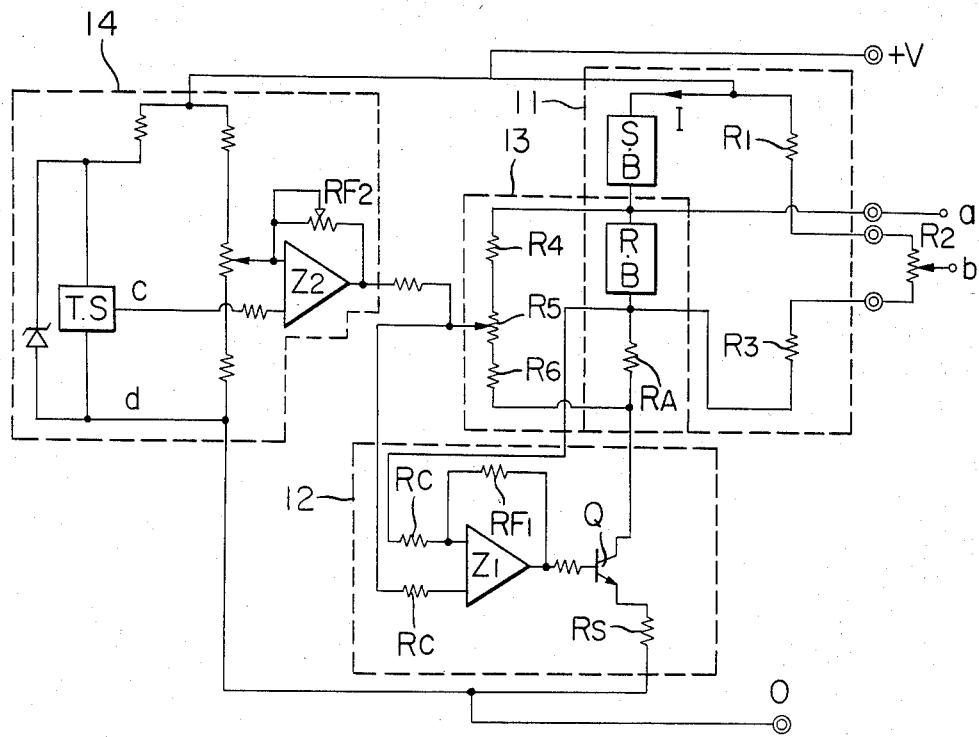
FIG. 5 is a diagram showing the circuit construction of the gas detecting portion of the gas detecting and monitoring device according to one embodiment of the present invention.

FIG. 5 schematically shows a circuit of the gas detecting portion of the gas detecting and monitoring device according to one embodiment of the present invention.

This gas detecting portion includes a bridge circuit 11, which is substantially same as that of the conventional device as described above and includes a gas detecting element consisting of a detecting element S.B and a compensating element R.B together with resistors $R_1$, $R_2$ and $R_3$ which are same as those included in the conventional device. Accordingly, further detailed description will not be given to the bridge circuit 11. A constant-current circuit 12, which corresponds to the constant-current circuit CR, included in the conventional device as described above, is arranged between the bridge circuit 11 and terminals +V and 0 of a power source. This constant-current circuit 12 is arranged to select a current passing through the detecting element S.B and hold it at a constant value in order that the temperature of the detecting element S.B many become maximum at some room temperature (for example, 20° C.), in the same manner as in the conventional device.

For example, the value of the current, when the temperature of the detecting element S.B becomes maximum, is set to 130–280 mA (130 mA at 20° C. for hydrogen gas and 275 mA at 20° C. for methane gas) in case where the detecting element is of catalytically-burning type, while said current value is set to 100–270 mA (270 mA at 20° C. for ammonia gas, and 265 mA at 20° C. for LP gas) in case where the detecting element is of semiconductor-adsorption type, and the constant-current circuit 12 is so constructed as to limit this current value within the range of ±3% of the above value. Now the operation of the constant-current circuit 12 will be explained. When the detecting element S.B detects the presence of an inflammable gas, the gas burns, so that the temperature of the detecting element itself becomes higher. (In case of methane gas, its temperature is 390° C. in air, while it becomes 450° C. in methane gas of 5% concentration). Accordingly, the resistance value of the platinum coil of the detecting element S.B increases, so that the current passing through the circuit decreases (275 mA→250 mA). In case of the compensating element R.B, the temperature of the element itself lowers and the voltage drop decreases, so that the bridge circuit becomes unbalanced. Thus the output current of the amplifier $Z_1$ is changed, thereby changing the conductivity of the transistor Q, so that the compensating element R.B is restored to its original value and consequently the current is restored. When the gas concentration decreases, the device operates conversely.

Even if the current passing through the element is held at a constant value by means of the constant-current circuit 12, the resistance value of the platinum wire coil of the element increases or decreases as the ambient temperature increases or decreases, as explained above, and the temperature of the element itself changes, that is, it is impossible to maintain a predetermined sensitivity. In order to provide compensation therefor, the present invention provides a compensating bridge circuit 13 which serves to hold the detecting element S.B and the compensating element R.B at constant values at all times, irrespective of the variation of the ambient temperature. The compensating bridge circuit 13 is formed by the compensating element R.B, a resistor $R_A$ and the resistors $R_4$, $R_5$ and $R_6$. The output of this compensating bridge circuit 13 is connected to the input of the amplifier $Z_1$ of the constant-current circuit 12, and the output of said amplifier $Z_1$ is connected to the base terminal of the transistor Q. In the embodiment as shown in FIG. 5, a fixed resistors having highly stable metal covering are used as the resistors $R_1$–$R_6$, $R_A$, $R_C$ and $R_F$ (their resistance temperature characteristic is +50 pp m/° C.).

Now the operation of the compensating bridge circuit 13, particularly the compensating element R.B., will be explained.

Figure 1:
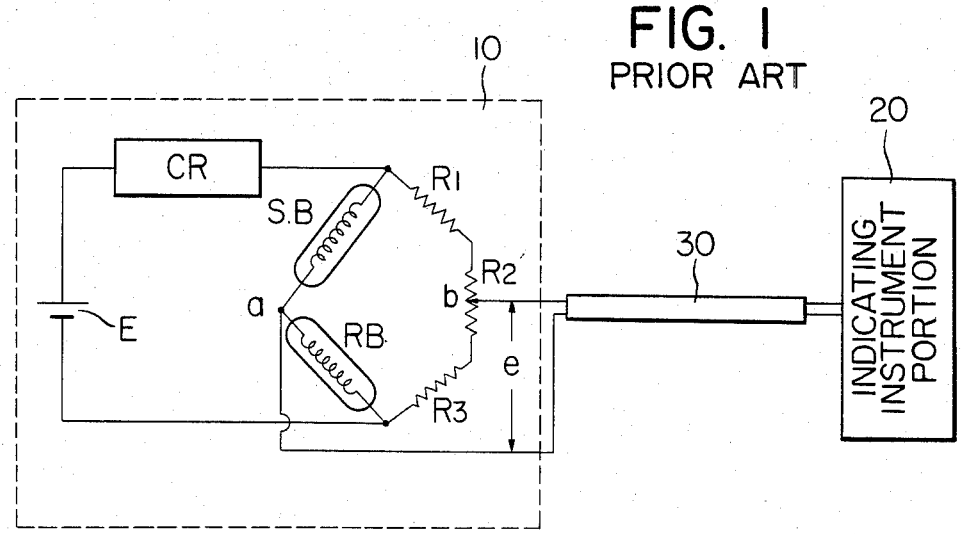
FIG. 1 is a diagram schematically showing the construction of an example of the conventional gas detecting and monitoring device.
Figure 2:
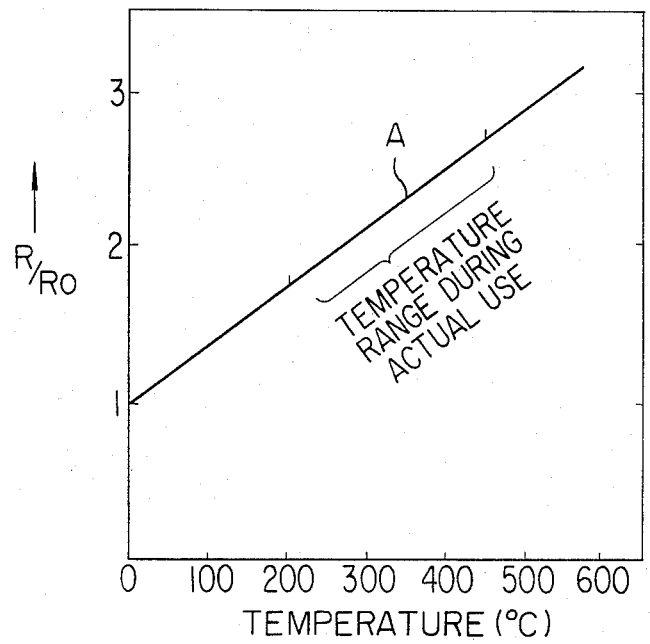
FIG. 2 is a diagram showing the temperature-resistance characteristic of the platinum wire.
Figure 3:
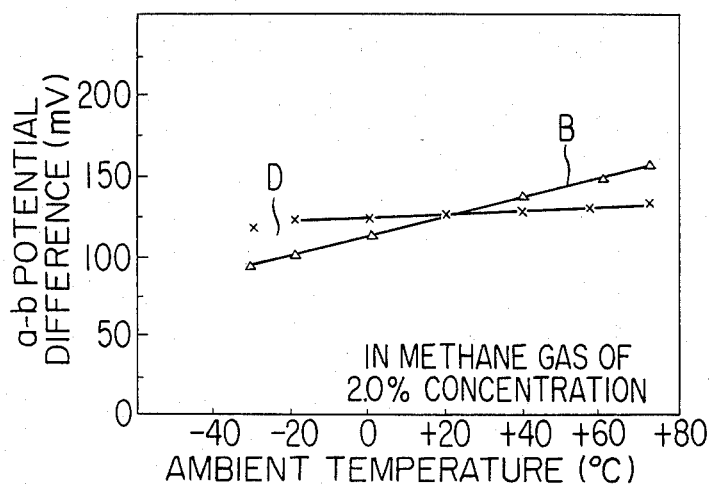
FIG. 3 is a diagram showing the gas sensitivity-temperature characteristic of the gas detecting and monitoring device.

(1) When the ambient temperature lowers:

The compensating element R.B decreases its resistance value by $\Delta RB_1$, as shown by the curve A in FIG. 2. Even if the current passing through the detecting element S.B and the compensating element R.B is controlled to a constant current by the constant-current circuit, the temperature of the element itself decreases by $I^2 \times \Delta RB_1$. When the subject gas exists in the air, the signal output of the bridge circuit 11 decreases if the compensating bridge circuit 13 is not provided. The curve B in FIG. 3 shows the change of the output of the bridge circuit 11 in the methane gas of 2.0% concentration, in case where the compensating bridge circuit 13 is not provided.

Then, the output of the compensating bridge circuit 13 makes substantially same change as that of the output of the bridge circuit 11, and this circuit serves to amplify such changing signal through the amplifier $Z_1$ and the transistor Q and feed $I + \Delta I_1$ (in case of the circuit for methane gas, I=275 mA at +20° C., and $\Delta I_1$=12 mA at −20° C. ) to the detecting element S.B, thereby holding the resistance of the element at a constant value.

(2) When the ambient temperature rises:

The compensating element R.B increases its resistance value by $\Delta RB_2$, as shown by the curve A in FIG. 2. Even if the current passing through the detecting element S.B and the compensating element R.B is controlled to a constant current by the constant-current circuit, the temperature of the element itself increases by $I^2 \times \Delta RB_2$. When the subject gas exists in the air, the signal output of the bridge circuit 11 increases if the compensating bridge circuit 13 is not provided. The curve B in FIG. 3 shows such change of output.

Then, the output of the compensating bridge circuit 13 makes substantially same change as that of the output of the bridge circuit 11, and this circuit serves to amplify such changing signal through the amplifier $Z_1$ and the transistor Q and feed $I - \Delta I^2$ (in case of the circuit for methane gas, I=275 mA at +20° C. and $\Delta I_2$ =11 mA at +60° C.) to the detecting element S.B, thereby holding the resistance of the element at a constant value.

Figure 4:
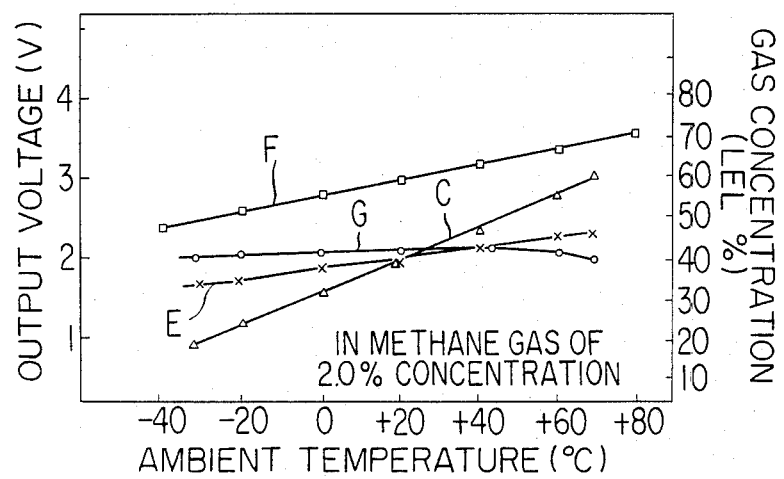
FIG. 4 is a diagram showing the relation between the ambient temperature and the indication error as seen on the indicating instrument of the gas detecting and monitoring device.

Owing to the operation of the compensating bridge circuit 13 as described above, the output of the bridge circuit 11 is improved, as shown by the curve D in FIG. 3. The curve D shows the relation between the gas sensitivity and the ambient temperature, expressed in the form of the relation between the a−b potential difference of the bridge circuit 11 and the ambient temperature. Such relation can be also expressed in the form of the relation between the ambient temperature and the indication error as seen on the indication of the instrument in the indicating instrument portion, such as shown by the curve E in FIG. 4. In the graph of FIG. 4, the scale at the right side indicates the values on the indicator at the indicating instrument portion. The gas concentration signal at the detecting portion is fed through the amplifier in the indicating instrument portion to said indicator and is indicated on said indicator in unit of LEL (low explosive level). In the embodiment, the bridge circuit 11 aims at limiting its output variation due to the ambient temperature change within 2% at the temperature range from +20° C. to +60° C.

Comparing the curves B and D and the curves C and E, it will be clear that the indication error depending on the ambient temperature change is considerably reduced by adding the compensating bridge circuit 13 according to the present invention.

As described above, the satisfactory compensation for the ambient temperature change at the detecting portion can be obtained by adding the compensating bridge circuit 13.

However, it will be understood from the curves D and E that the output of the bridge circuit 11 still varies slightly depending upon the ambient temperature change. This is due to change of the characteristics of the parts depending upon the ambient temperature change, and such an output variation cannot be fully compensated for only by adding the compensating bridge circuit 13.

Under such circumstances, the embodiment as shown in FIG. 5 further provides the compensation for changes of the characteristics of the parts depending upon the ambient temperature change, such as slight error of resistance value of the detecting and compensating elements (allowance ±2%), irregularities in resistance-temperature characteristics of the respective resistors, slight temperature error according to the temperature characteristics of 1C and transistors, drift or the like, by arranging a correcting circuit 14 near the detecting element S.B and the compensating element R.B. This correcting circuit 14 includes, as its main components, a temperature sensor T.S and an amplifier $Z_2$, the output of which is connected to the sliding contact of the resistor $R_5$ of the compensating bridge circuit 13. The temperature sensor T.S consists of a semiconductor sensor, for example, which is arranged near the detecting element S.B and produces an output which is proportional to the ambient temperature change. The curve F in FIG. 4 shows temperature-output characteristic of this temperature sensor T.S. The scale at the left side of FIG. 4 indicates an output voltage between c and d of the temperature sensor T.S in the circuit shown in FIG. 5. The temperature sensor T.S is of a commercially availabel 1C type, in which constant voltage of DC 6.85 V is applied thereto and the output voltage obtained at the terminals c-d is:

| | |
|---|---|
| T = −25° C. | DC 2.48 V |
| T = +25° C. | DC 2.98 V |
| T = +85° C. | DC 3.58 V |

This is a highly precise sensor, having linearity 0.5%, reproducibility 0.3% and linear output voltage 10 mV/° C. The output of this temperature sensor T.S is connected through the amplifier $Z_2$ to the compensating bridge circuit 13 to feed its output current (0.2–0.6 mA) to the sliding contact of the resistor $R_5$ of said compensating bridge circuit 13, thereby finely correcting the relation of a part of $R_4+R_5$, a part of R.B and $R_6+R_5$ and $R_4$ in the compensating bridge circuit 13. By the adjustment of the resistor $RF_2$ of the amplifier $Z_2$, the gradient of the output can be selected.

By the operation as described above, the indication error as indicated by the curve E in FIG. 4 can be improved as shown by the curve G. For example, the indication error depending upon the ambient temperature change could be limited into the range of ±2%.

Figure 6:
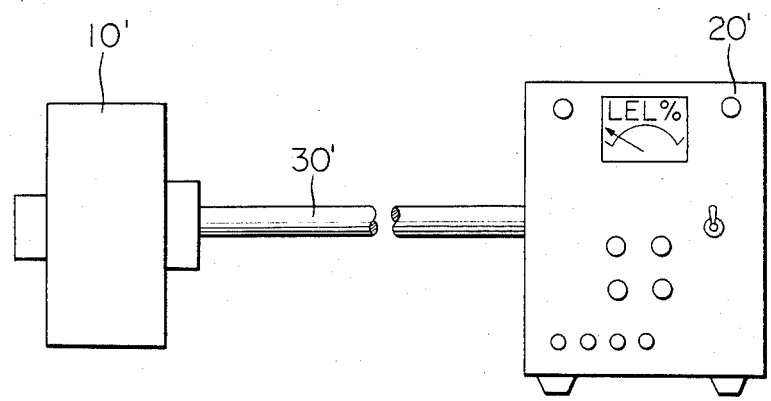
FIG. 6 is a view showing the construction of the whole body of the gas detecting and monitoring device according to one embodiment of the present invention.

FIG. 6 schematically shows the whole body of the gas detecting and monitoring device. In this device, the circuit of the gas detecting part as shown in FIG. 5 is contained in a gas detecting portion 10' which is separately formed from an indicating instrument portion 20', and the gas detecting portion 10' and the indicating instrument portion 20' can be connected together, if necessary, by a transmission cable having length about 10-2000 m. In consideration of change of the characteristics of the detecting element and change of the characteristics of the parts depending on the ambient temperature change, as afore-described, it is preferable in view of precision to collectively house all of the detecting element, the compensating elements and the other parts required for the detection into the gas detecting portion 10' and to transmit the final signal to the indicating instrument portion 20' by means of the transmission cable 30'. In such case, it is further preferable to arrange the circuit components on a printed circuit board and house it in the space in the gas detecting portion. With regard to the indicating instrument portion 20', it is preferable to collectively house the indicators together with the parts for effecting connection of power source, zero adjustment, setting of values, dispatch of alarm signal or the like into said indicating instrument portion.

In the embodiment as described above, the element of catalytically-burning type is used as the detecting element. However, the present invention can be applied, with same effect, to the device in which the other type of detecting element is used. For example, a semiconductor type detecting element which comprises a platinum wire coil having MOS sintered thereon and another platinum wire passing through the center of said coil, without contacting said coil, and forming an electrode at its one end can be effectively used in the device according to the present invention.

I claim:

1. A gas detecting and monitoring device having a bridge circuit including a gas detecting element and a constant-current circuit for feeding a constant current to said gas detecting element, characterized in that said bridge circuit comprises a compensating bridge circuit including at least a part of said gas detecting element, said compensating bridge circuit producing a signal corresponding to the variation of the resistance value of said gas detecting element depending upon the variation of the ambient temperature and feeding said signal to said constant-current circuit to automatically control the current fed to said bridge circuit thereby maintaining the resistance value of said gas detecting element at a constant value, and a correcting circuit including a temperature sensor for sensing the variation of the ambient temperature disposed near said gas detecting element, said correcting circuit feeding the output of said temperature sensor corresponding to the variation of the ambient temperature to said compensating bridge circuit thereby compensating for the variation of the respective circuit components owing to the variation of the ambient temperature.

2. A gas detecting and monitoring device as claimed in claim 1 wherein said gas detecting element consists of a detecting element and a compensating element and said at least a part of said gas detecting element is said compensating element.

3. A gas detecting and monitoring device as claimed in claim 2 wherein said temperature sensor of said correcting circuit is disposed near said detecting element of said gas detecting element.

4. A gas detecting and monitoring device as claimed in claim 1 or 2 or 3 wherein said constant-current circuit includes a transistor for controlling the current flow through said gas detecting element and an amplifier for controlling at the conductivity of said transistor, and the output of said compensating bridge circuit is coupled to the input of said amplifier to thereby control the conductivity of said transistor.

5. A gas detecting and monitoring device as claimed in claim 1 or 2 or 3 wherein said correcting circuit includes an amplifier which receives a signal from said temperature sensor to produce an output according to said signal and to be applied to said compensating bridge circuit.

6. A gas detecting and monitoring device comprising a pair of terminals for power source, a gas detecting bridge circuit (11) having a pair of input terminals connected to said power source terminals and a pair of output terminals across which a gas detection signal is generated and including a gas detecting element consisting of a detecting element (S.B) and a compensating element (R.B), and a constant-current circuit (12) for feeding a constant current to said detecting element (S.B) and said compensating element (R.B) at a predetermined temperature, characterized in that said device comprises a compensating bridge circuit (13) including said compensating element (R.B) and having a pair of output terminals, said compensating bridge circuit (13) producing a resistance variation signal across the pair of output terminals, said resistance variation signal corresponding to the variations of the resistance values of said detecting element (S.B) and said compensating element (R.B) depending upon the variation of the ambient temperature from said predetermined temperature, said constant-current circuit (12) comprising a transistor (Q) connected between said input terminals of said gas detecting bridge circuit (11) and said power source terminals for controlling the current flow through said detecting element (S.B) and said compensating element (R.B) and a first amplifier ($Z_1$) having an input coupled across said pair of output terminals of said compensating bridge circuit (13) for producing an output responsive to said resistance variation signal and applying said output to said transistor (Q) to control the conductivity of said transistor (Q), whereby the current flow through said detecting element (S.B) and said compensating element (R.B) increases or decreases from said constant current value so that the resistances of said detecting element (S.B) and said compensating element (R.B) are kept constant even if the ambient temperature changes from said predetermined temperature, and said gas detecting and monitoring device further comprising a correcting circuit (14) for compensating for changes in the characteristics of the respective circuit components including said detecting element (S.B.) and said compensating element (R.B) of said circuits (1, 12 and 13) owing to the variation of the ambient temperature, said correcting circuit (14) comprising a temperature sensor (T.S) disposed near said detecting element (S.B) for producing an output proportional to the variation of the ambient temperature and a second amplifier ($Z_2$) for amplifying said output of said temperature sensor (T.S) and applying the amplified output to the junction of said output terminals of said compensating bridge circuit (13) and said input of said first amplifier ($Z_1$) of said constant-current circuit (12), said second amplifier ($Z_2$) amplifying the output of said temperature sensor (T.S) in such a manner that said increase or decrease from said constant current by said compensating bridge circuit (13) is further adjusted, thereby suppressing any error in said gas detection signal as would be caused by the changes in the characteristics of the respective circuit components owing to the variation of the ambient temperature.

7. A gas detecting and monitoring device as claimed in claim 6 wherein said second amplifier ($Z_2$) is provided with a variable resistor ($RF_2$) for selectively adjusting the gradient of the output of the second amplifier ($Z_2$).

8. A gas detecting and monitoring device as claimed in claim 6 or 7 wherein said constant-current circuit includes a transistor for controlling the current flow through said gas detecting element and an amplifier for controlling the conductivity of said transistor, and the output of said compensating bridge circuit is coupled to the input of said amplifier to thereby control the conductivity of said transistor.

* * * * *